United States Patent [19]
Tregillis

[11] Patent Number: 5,338,190
[45] Date of Patent: Aug. 16, 1994

[54] DENTAL APPLIANCE

[75] Inventor: John S. Tregillis, Coon Rapids, Minn.

[73] Assignee: Sentage Corporation, Minneapolis, Minn.

[21] Appl. No.: 50,808

[22] Filed: Apr. 22, 1993

[51] Int. Cl.$^5$ .............................................. A61C 3/00
[52] U.S. Cl. ...................................................... 433/6
[58] Field of Search .......................... 433/6, 215, 48; 128/861, 862

[56] References Cited

U.S. PATENT DOCUMENTS

| | | | |
|---|---|---|---|
| 3,211,143 | 10/1965 | Grossberg | 128/862 |
| 3,314,423 | 4/1967 | Boatwright et al. | 128/861 |
| 3,921,292 | 11/1975 | Ivchenko | 32/2 |
| 3,950,851 | 4/1976 | Bergersen | 433/6 |
| 3,969,303 | 7/1976 | Prosen | 260/31.8 |
| 4,073,061 | 2/1978 | Bergersen | 433/6 |
| 4,160,065 | 7/1979 | Gigante | 32/2 |
| 4,529,777 | 7/1985 | Daidone | 525/193 |
| 4,568,558 | 2/1986 | Angrick et al. | 427/2 |
| 4,656,053 | 4/1987 | Angrick et al. | 427/53.1 |
| 4,746,469 | 5/1988 | Yamashita | 264/18 |
| 4,838,789 | 6/1989 | Tanaka et al. | 433/171 |
| 4,892,478 | 1/1990 | Tateosian et al. | 433/6 |

Primary Examiner—Cary E. O'Connor
Attorney, Agent, or Firm—Hugh D. Jaeger

[57] ABSTRACT

A dental appliance including a heat-cured methyl methacrylate and a heat-cured ethyl acrylate. The heat-cured methyl methacrylate covers the occlusal surface of the teeth, while the heat-cured ethyl acrylate covers the buccal side and lingual side of the teeth and may extend onto the tissue. The occlusal surface remains hard. The dental appliance can be a splint, such as for bruxism, temporomandibular disorders, or mandibular repositioning appliances.

3 Claims, 1 Drawing Sheet

DENTAL APPLIANCE

BACKGROUND OF THE INVENTION

1. Field of the Invention

The present invention relates to a dental appliance, and more particularly, pertains to a dental appliance of a heat-cured methyl methacrylate and heat-cured ethyl acrylate combined to form a dental splint.

2. Description of the Prior Art

Prior art dental appliances only cover the clinical crown of the teeth, which can be discomforting to a patient. Prior art appliances had either soft occlusal surfaces, which patients would some times chew through, or would fracture frequently.

The present invention overcomes the disadvantages of the prior art by providing a dental appliance which provides for patient comfort, and covers more than the clinical crown of the teeth.

SUMMARY OF THE INVENTION

The general purpose of the present invention is a dental appliance with a heat-cured methyl methacrylate covering the occlusal surface of the teeth and heat-cured ethyl acrylate on the buccal (cheek side) and the lingual (tongue side) of the teeth. The lingual coverage also extends down beyond the crown of the teeth for additional retention and patient comfort.

According to one embodiment of the present invention, there is provided a dental appliance including a heat-cured methyl methacrylate covering the occlusal surface of the teeth and heat-cured ethyl acrylate covering either or both of the buccal side of the teeth and the lingual side of the teeth where the extension of coverage is for added retention and patient comfort. The dental appliance is constructed using a lost wax technique, as later described in detail. The dental appliance can be utilized as a night guard, bruxism splint, T.M.D. appliance, or functional orthodontic appliances and can be made for either dental arch, upper or lower.

Significant aspects and features of the present invention for the patient are:

Biocompatibility, where the appliance fits even after extended periods of non-use.

Comfortability where the appliance causes no pressures to be exerted on teeth.

No clasping of the appliance is necessary.

The appliance does not wear as fast as a resilient splint (i.e. Brux-eze); and therefore, is ideal for heavy bruxer or clencher.

Significant aspects and features of the present invention for the doctor are:

Ease of delivery in that no teeth or tissue side adjustments are necessary.

No change in clinical procedures are required.

The appliance lends itself to all philosophies of treatment.

The appliance offers high patient compliance.

The appliance lasts longer for heavy bruxers and/or clenchers.

Having thus described embodiments of the present invention, it is one object of the present invention to provide a dental appliance including a heat-cured methyl methacrylate for covering the occlusal surface of the teeth and a heat-cured ethyl acrylate for covering the sides of the teeth, as well as extending and covering portions of the tissue as necessary.

One object of the present invention is a dental appliance which can be fashioned and formed as a night guard, bruxism splint, T.M.D. appliance, or functional orthodontic appliance.

Another object of the present invention is a dental appliance which provides for added retention and patient comfort.

A further object of the present invention is a dental appliance which covers the crown of the teeth and can extend into the lingual vestibule or palatal vault, and can also extend into the tissue undercuts on the buccal when deemed necessary.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
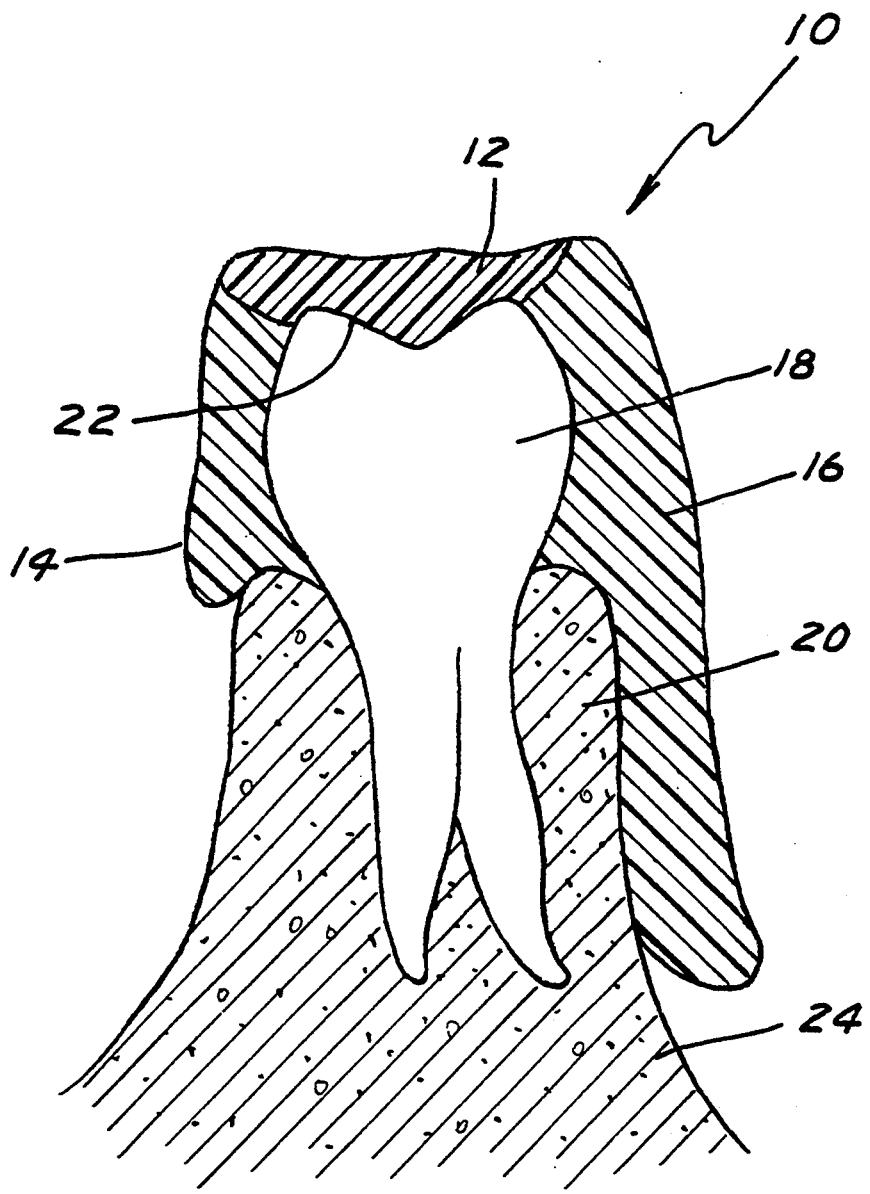
FIG. 1 illustrates a cross-sectional view of a dental appliance, the present invention, about a teeth and tissue.

FIG. 1 illustrates a cross-sectional view of a dental appliance 10, the present invention, surrounding a teeth 18 in a gum 20. The dental appliance 10 includes a heat-cured methyl methacrylate 12 covering the occlusal surface 22 of the teeth 18, and heat-cured ethyl acrylates 14 and 16 covering the buccal 24 and the lingual 26, respectively. Borders of the appliance can extend into the tooth undercuts on the buccal and can extend deep into the lingual vestibule. The particular shaping and form of the dental appliance 10 determines whether the dental appliance is used as a night guard, a bruxism splint, a TMD appliance, or a functional orthodontic appliance.

MODE OF OPERATION

The dental appliance 10 of the present invention is constructed according to the following steps by way of example and for purposes of illustration only and not to be construed as limiting of the present invention:

1. Wax, invest and boil out as one would for a splint.

2. After boiling out, a silicone shim is fashioned to fit the occlusal portion of the top half of the flask. The overall thickness of the shim should be dimensioned slightly more than the occlusal thickness of the splint.

3. While the shim is still soft, squeeze the two halves of the flask together. All teeth should indent the shim.

4. The shim represents the area of hard acrylic (methyl methacrylate) on the finished appliance, and should be the full width of the occlusion. Care must be taken not to apply the hard acrylic to the buccal or lingual sides of the teeth or tissue.

5. The ethyl acrylate material is mixed in a 3:1 powder to liquid ratio. The trial pack is accomplished while the material is soft so as not to displace the shim. A separator sheet is used between the ethyl acrylate material and the shim.

6. Heat cure the ethyl acrylate under pressure at 205° F. for a minimum of 20 minutes, maximum of 30 minutes.

7. Open the flask and discard the silicone shim and refrigerate at 32° F. or less for 15 minutes.

8. When the ethyl acrylate has stiffened to a stage that it is nondisplaceable, pack the portion of the mold previously occupied by the silicon shim (the methyl methacrylate) and cure in a usual manner. There is a chemical bond achieved while the appliance is cured under heat and pressure.

The use of the dental appliance is determined by the particular application of the dentist or the orthodontist.

Various modifications can be made to the present invention without departing from the apparent scope hereof.

I claim:

1. A dental appliance comprising:

a. a heat-cured methyl methacrylate for covering an occlusal surface of the teeth; and, b. a heat-cured ethyl acrylate chemically bonded to said methyl methacrylate for covering at least one side surface of the teeth.

2. The process for making a dental appliance comprising the steps of:

heat curing methyl methacrylate for covering an occlusal surface of the teeth; and, b. heat curing a ethyl acrylate and forming a chemical bond to said methyl methacrylate to cover at least one side surface of the teeth.

3. The product of a splint formed by the process of claim 2.

* * * * *